(12) United States Patent
Vittur et al.

(10) Patent No.: US 7,918,889 B2
(45) Date of Patent: Apr. 5, 2011

(54) EXPANDABLE SPINAL PROSTHETIC DEVICES AND ASSOCIATED METHODS

(75) Inventors: Shannon M. Vittur, Memphis, TN (US); Lukas Eisermann, San Diego, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1136 days.

(21) Appl. No.: 11/362,998

(22) Filed: Feb. 27, 2006

(65) Prior Publication Data
US 2007/0203579 A1    Aug. 30, 2007

(51) Int. Cl.
*A61F 2/44* (2006.01)
(52) U.S. Cl. ................................. 623/17.15
(58) Field of Classification Search ..... 623/17.11–17.16
See application file for complete search history.

(56) References Cited

U.S. PATENT DOCUMENTS

| | | | |
|---|---|---|---|
| 2,182,673 A * | 12/1939 | Magnano | 81/436 |
| 3,875,595 A | 4/1975 | Froning | |
| 4,772,287 A | 9/1988 | Ray et al. | |
| 4,863,477 A | 9/1989 | Monson | |
| 4,904,260 A | 2/1990 | Ray et al. | |
| 5,047,055 A | 9/1991 | Bao et al. | |
| 5,146,933 A | 9/1992 | Boyd | |
| 5,171,280 A | 12/1992 | Baumgartner | |
| 5,334,626 A * | 8/1994 | Lin | 523/116 |
| 5,344,459 A | 9/1994 | Swartz | |
| 5,425,773 A * | 6/1995 | Boyd et al. | 623/17.15 |
| 5,522,898 A | 6/1996 | Bao | |
| 5,549,679 A | 8/1996 | Kuslich | |
| 5,562,736 A | 10/1996 | Ray et al. | |
| 5,571,189 A | 11/1996 | Kuslich | |
| 5,645,597 A | 7/1997 | Krapiva | |
| 5,705,780 A | 1/1998 | Bao | |
| 5,755,797 A | 5/1998 | Baumgartner | |
| 5,824,093 A | 10/1998 | Ray et al. | |
| 5,888,220 A | 3/1999 | Felt et al. | |
| 5,919,235 A | 7/1999 | Husson et al. | |
| 5,928,284 A | 7/1999 | Mehdizadeh | |
| 5,976,189 A | 11/1999 | Keller | |
| 6,022,376 A * | 2/2000 | Assell et al. | 623/17.16 |
| 6,140,452 A | 10/2000 | Felt et al. | |
| 6,146,422 A | 11/2000 | Lawson | |
| 6,165,218 A | 12/2000 | Husson et al. | |
| 6,183,518 B1 | 2/2001 | Ross et al. | |

(Continued)

FOREIGN PATENT DOCUMENTS

WO      WO9846169 A      10/1998

(Continued)

OTHER PUBLICATIONS

European Patent Office, International Searching Authority,Notification of Transmittal of the International Search Report and the Written Opinion of the International Searching Authority or the Declaration, International Application No. PCT/US2007/062372, Jul. 27, 2007, 7 pages.

*Primary Examiner* — Anu Ramana

(57) ABSTRACT

A prosthetic device for insertion into an intervertebral space defined by adjacent vertebrae includes a first articulation member and a second articulation member configured to cooperate to permit articulating motion. An expandable member may be connected to the first articulation member and may be configured to support and position the first articulation member within the intervertebral space.

14 Claims, 8 Drawing Sheets

U.S. PATENT DOCUMENTS

| | | |
|---|---|---|
| 6,206,921 B1 | 3/2001 | Guagliano et al. |
| 6,231,609 B1 | 5/2001 | Mehdizadeh |
| 6,248,131 B1 | 6/2001 | Felt et al. |
| 6,264,695 B1 | 7/2001 | Stoy |
| 6,306,177 B1 | 10/2001 | Felt et al. |
| 6,375,682 B1 | 4/2002 | Fleischmann et al. |
| 6,402,750 B1 | 6/2002 | Atkinson et al. |
| 6,402,784 B1 | 6/2002 | Wardlaw |
| 6,419,704 B1 | 7/2002 | Ferree |
| 6,482,234 B1 | 11/2002 | Weber et al. |
| 6,517,580 B1 * | 2/2003 | Ramadan et al. .......... 623/17.15 |
| 6,602,291 B1 | 8/2003 | Ray et al. |
| 6,610,094 B2 | 8/2003 | Husson |
| 6,645,248 B2 | 11/2003 | Gasutt |
| 6,692,495 B1 | 2/2004 | Zacouto |
| 6,733,533 B1 | 5/2004 | Lozier |
| 6,783,546 B2 | 8/2004 | Zucherman et al. |
| 6,827,743 B2 | 12/2004 | Eisermann et al. |
| 6,835,205 B2 | 12/2004 | Atkinson et al. |
| 6,893,465 B2 | 5/2005 | Huang |
| 6,958,077 B2 | 10/2005 | Suddaby |
| 7,235,104 B2 * | 6/2007 | Grinberg et al. ........... 623/17.14 |
| 7,563,286 B2 * | 7/2009 | Gerber et al. .............. 623/17.14 |
| 2001/0004710 A1 | 6/2001 | Felt et al. |
| 2001/0049527 A1 | 12/2001 | Cragg |
| 2002/0016583 A1 | 2/2002 | Cragg |
| 2002/0026195 A1 | 2/2002 | Layne et al. |
| 2002/0049498 A1 | 4/2002 | Yuksel et al. |
| 2002/0059001 A1 | 5/2002 | Yuksel et al. |
| 2002/0107573 A1 | 8/2002 | Steinberg |
| 2002/0177866 A1 | 11/2002 | Weikel et al. |
| 2003/0040802 A1 * | 2/2003 | Errico et al. ............... 623/17.14 |
| 2003/0074075 A1 | 4/2003 | Thomas, Jr. et al. |
| 2003/0074076 A1 | 4/2003 | Ferree et al. |
| 2003/0083642 A1 | 5/2003 | Boyd et al. |
| 2003/0135278 A1 * | 7/2003 | Eckman .................... 623/17.14 |
| 2004/0024463 A1 | 2/2004 | Thomas, Jr. et al. |
| 2004/0054413 A1 | 3/2004 | Higham et al. |
| 2004/0073308 A1 | 4/2004 | Kuslich et al. |
| 2004/0093087 A1 | 5/2004 | Ferree et al. |
| 2004/0102774 A1 | 5/2004 | Trieu |
| 2004/0133280 A1 | 7/2004 | Trieu |
| 2004/0186471 A1 | 9/2004 | Trieu |
| 2004/0186576 A1 | 9/2004 | Biscup et al. |
| 2004/0193273 A1 | 9/2004 | Huang |
| 2004/0210297 A1 | 10/2004 | Lin et al. |
| 2004/0215342 A1 | 10/2004 | Suddaby |
| 2004/0220296 A1 | 11/2004 | Lowman et al. |
| 2004/0220582 A1 * | 11/2004 | Keller .............................. 606/99 |
| 2005/0049707 A1 | 3/2005 | Ferree |
| 2005/0060036 A1 | 3/2005 | Schultz et al. |
| 2005/0090901 A1 | 4/2005 | Studer |
| 2005/0143749 A1 * | 6/2005 | Zalenski et al. ................. 606/99 |
| 2005/0187631 A1 * | 8/2005 | Van Hoeck et al. ........ 623/17.13 |
| 2005/0197702 A1 | 9/2005 | Coppes et al. |
| 2005/0209601 A1 | 9/2005 | Bowman et al. |
| 2005/0209602 A1 | 9/2005 | Bowman et al. |
| 2006/0015183 A1 | 1/2006 | Gilbert et al. |
| 2006/0084988 A1 * | 4/2006 | Kim ............................... 606/61 |
| 2007/0150059 A1 * | 6/2007 | Ruberte et al. ............. 623/17.12 |

FOREIGN PATENT DOCUMENTS

WO  WO2005107654 A  11/2005

* cited by examiner

EXPANDABLE SPINAL PROSTHETIC DEVICES AND ASSOCIATED METHODS

BACKGROUND

Disc arthroplasty is one way of treating injured, degraded, or diseased spinal joints. Some disc arthroplasty treatments include replacing injured discs of the joint with a motion-preserving spinal disc that allows some articulation or movement of the spinal joint. While the inserted disc may provide joint articulation to a patient, inserting the spinal disc can be an invasive and intensive procedure. For example, conventional spinal discs are fairly large and; therefore, may typically be installed through an anterior procedure. Because anterior procedures often require displacement of vessels, such as the aorta and vena cava, they must be performed with great care. Further, because scar tissue may grow about the surgical site, any required second treatment can be more difficult, and may introduce additional distress to the patient.

What is needed is a prosthetic device for insertion into an intervertebral space that may have a smaller geometry than conventional discs, providing surgical options to a physician. The current disclosure overcomes one or more problems in the prior art.

SUMMARY

In one exemplary aspect, this disclosure is directed to a prosthetic device for insertion into an intervertebral space defined by adjacent vertebrae. In one aspect, the prosthetic device includes an expandable support. For example, the prosthetic device may include a first articulation member having a first articulating surface and a first attachment surface. It may also include a second articulation member having a second articulating surface and a second attachment surface. The second articulating surface may be configured to cooperate with the first articulating surface to permit articulating motion. A connecting means may be configured to selectively secure a first articulation member relative to a second articulation member. An expandable member may be connected to the first articulation member and may be configured to support and position the first articulations member within the intervertebral space.

In another exemplary aspect, this disclosure is directed to a method of inserting a prosthetic device into an intervertebral space defined by adjacent vertebrae. The method may include placing a first articulation member having a first articulating surface and a first attachment surface in the intervertebral space with a first instrument. A second articulation member having a second articulating surface and a second attachment surface may also be placed in the intervertebral space with a second instrument. An expandable member connected to the first articulation member to support and position the first articulation member may be expanded such that the first articulating surface and the second articulating surface cooperate to permit articulating motion.

DETAILED DESCRIPTION

Figure 1:
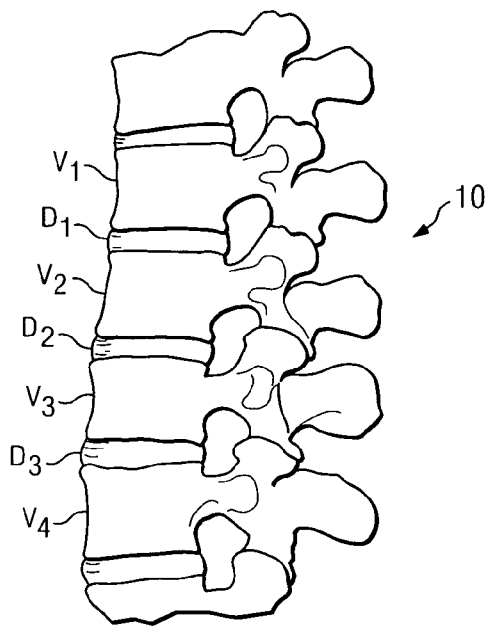
FIG. 1 is a pictorial representation of a lateral view of a portion of a vertebral column.

The present invention relates generally to vertebral reconstructive devices, and more particularly, to an articular disc device for implantation. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebrae.

Figure 2:
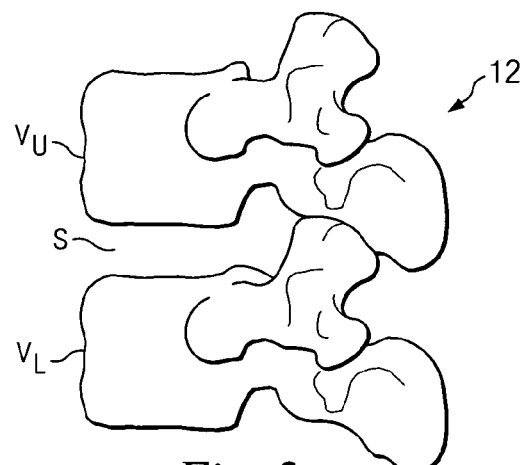
FIG. 2 is a pictorial representation of a lateral view of a pair of adjacent vertebral bodies defining an intervertebral space.

For the sake of further example, two of the vertebrae will be discussed with reference to FIG. 2. The two vertebrae form a spinal motion segment 12 including a lower vertebrae $V_L$ and an upper vertebrae $V_U$. Some types of disc arthroplasty require that some or all of the natural disc that would have been positioned between the two vertebrae $V_L$, $V_U$ be removed via a discectomy or a similar surgical procedure. Removal of the diseased or degenerated disc results in the formation of an intervertebral space S between the upper and lower vertebrae $V_U$, $V_L$. Although the illustration of FIG. 2 generally depicts the vertebral joint 12 as a lumbar vertebral joint, it is understood that the devices, systems, and methods of this disclosure may also be applied to all regions of the vertebral column, including the cervical and thoracic regions. Furthermore, the devices, systems, and methods may be used in other regions of the spine, such as, for example, the facet joints. In this disclosure, use of the term intervertebral disc space may also include the facet joints.

Conventional prosthetic devices have a fixed geometry. Therefore, insertion of a conventional device into the intervertebral space S requires space enough to insert the prosthetic device, and in addition, room to manipulate it. Accordingly, relatively large openings and invasive procedures are required for insertion of a conventional prosthetic disc. However, the articular device disclosed herein may require a smaller opening and less invasive procedures because the geometry of the prosthetic device is not entirely fixed prior to implantation. Instead, the articular device incorporates at least one expandable member, such a sack or bag, that can be introduced in the intervertebral space S in a small, deflated state. Once in place, the bag may be expanded in-situ to form the articular device. Because the geometry is not fixed until after the prosthetic device is placed into the vertebral space S, the prosthetic device may have a smaller profile than conventional discs. Further, because it is not fixed, the profile of the prosthetic device may be readily manipulated if required during insertion. A smaller, malleable profile may allow an operating physician to install the prosthetic device using less invasive installation techniques. For example, instead of being required to install the disc anteriorly, the physician may have the option to install the disc through an alternate direction, such as from a posterior, anterior oblique, or lateral approach to the spine. This may give physicians more options in installation, and may allow the physician to perform less invasive and less distressing procedures.

Further, because the articular device disclosed herein may allow a surgeon to manipulate the location of the articular couple within the disc space. For example, a surgeon may be allowed to position the articular couple, even after preparation and placement of the device. Accordingly, the surgeon may more easily place the device with the articular couple at an ideal center of rotation because the articular surface is not attached to rigid endplates.

Figure 3:
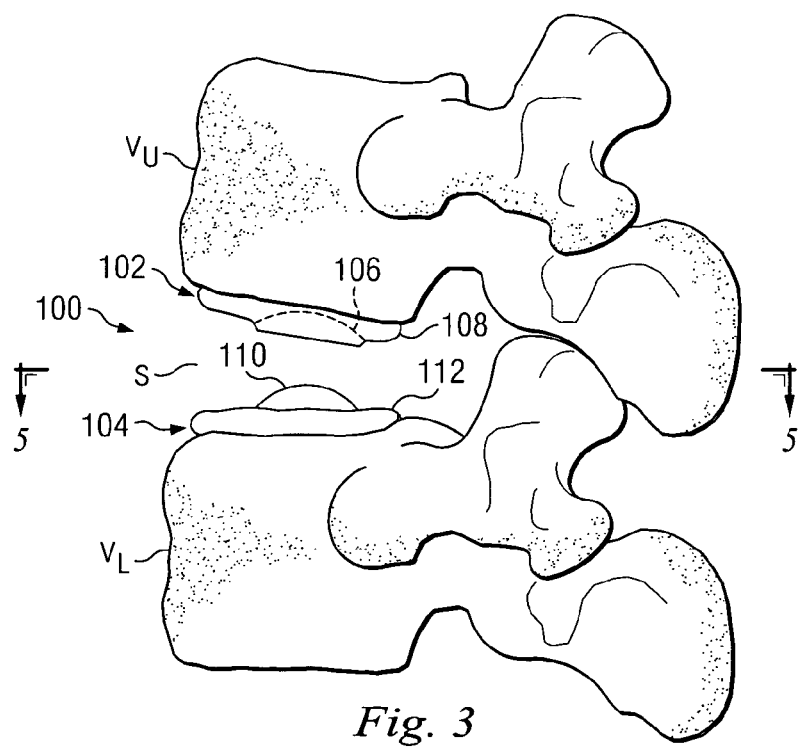
FIG. 3 is a pictorial representation of an intervertebral prosthetic device disposed between adjacent vertebral bodies.

FIG. 3 shows one exemplary embodiment of a prosthetic device 100 in an intervertebral disc space S. In FIG. 3, the upper and lower vertebrae $V_U$, $V_L$ are shown spaced apart an exaggerated amount to show the components of the prosthetic device 100 in greater detail. The prosthetic device 100 includes a top portion 102 and a bottom portion 104. The top portion 102 may include a top articulation member 106 and a top expandable member 108. Similarly, the bottom portion 104 may include a bottom articulation member 110 and a bottom expandable member 112.

Figure 4:
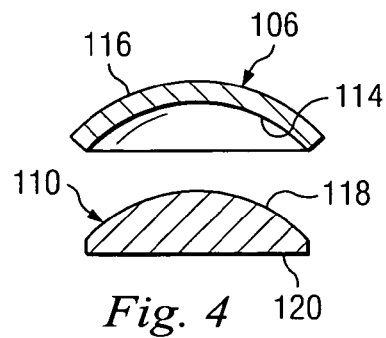
FIG. 4 is a pictorial representation of a partial cross-sectional view of articulation members of the intervertebral prosthetic device of FIG. 3.

FIG. 4 shows a partial cross-sectional view of the articulation members 106, 110 independent from the expandable members 108, 112. The top and bottom articulation members 106, 110 may be configured to cooperate together to provide articulation to the prosthetic device 100 and to allow articulation of the upper vertebrae $V_U$ relative to the lower vertebrae $V_L$. FIGS. 3 and 4 show the upper and lower vertebrae $V_U$, $V_L$ and the prosthetic device 100 spaced apart. Although not shown in FIGS. 3 and 4, the top articulation member 106 is intended to cooperate with the bottom articulation member 110 to form an articulating joint. In one exemplary embodiment, the top articulation member 106 includes a spherical concave recess forming a socket while the bottom articulation member 110 includes a convex bearing surface forming a ball, together forming a ball and socket joint.

The top and bottom articulation members 106, 110 may be preformed members made by, for example, forming or molding processes, and may be formed of any rigid material allowing articulation between the respective members. In one exemplary embodiment, the top and bottom articulation members 106, 110 are formed of a biocompatible metal, such as, for example, stainless steel, cobalt chrome, or titanium, among others. In other embodiments, the top and bottom articulation members 106, 110 may be formed of a biocompatible ceramic material or a polymer material, such as polyethylene and carbon fiber reinforced PEEK that may be optionally combined with metal or ceramic. Other suitable materials also may be used.

Referring to the cross-sectional view of FIG. 4, each articulation member 106, 110 includes an articulating surface 114, 118, respectively, and an attachment surface 116, 120, respectively. The articulating surfaces 114, 118 may cooperate to provide the articulation. In one exemplary embodiment, the articulating surfaces 114, 118 may be smooth or polished in order to promote low friction articulation. The attachment surfaces 116, 120 of the articulation members 106, 110 may be configured to engage and attach to the top expandable member 108 and the bottom expandable member 112, respectively.

Figure 5:
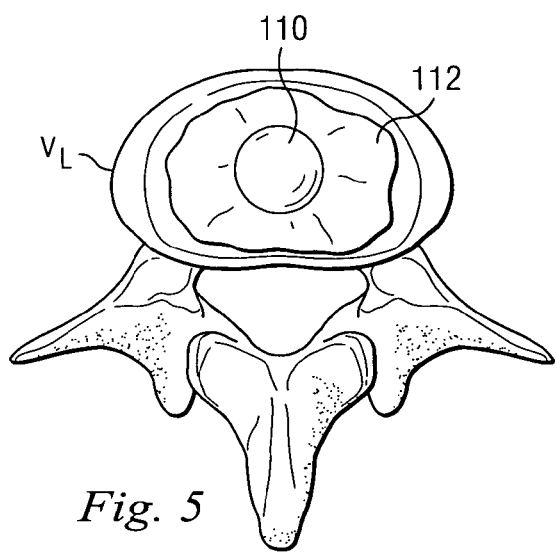
FIG. 5 is a pictorial representation of a top view of a part of the intervertebral prosthetic device of FIG. 3 on a lower vertebral body.

As shown in FIGS. 3 and 5, the top expandable member and the bottom expandable member may be respectively attached to the top and bottom articulation members 106, 110. This attachment may be performed in any suitable manner. In one exemplary embodiment, the articulation members 106, 110 are respectively adhered to the expandable members 108, 112 using an adhesive. In another exemplary embodiment, the articulation members 106, 110 are adhered to the expandable members 108, 112 using a woven method where sutures connect the articulation members 106, 110 and the expandable members 108, 112. In yet another exemplary embodiment, the articulation members 106, 110 may be secured to the respective expandable members 108, 112 using a tacking or pin system. In this exemplary embodiment, tacks (not shown) may be secured to or formed upon the articulation member. The tack may then extend through the expandable member and may be secured inside the expandable member to connect the articulation member and expandable member. Other methods also may be used.

The top and bottom expandable members 108, 112 may be comprised of biocompatible sacks capable of being filled with a filling material. In one exemplary embodiment, the top and bottom expandable members 108, 112 may be comprised of a woven material as described in U.S. Pat. No. 6,827,743, which is incorporated herein in its entirety by reference. When in an un-expanded state, the expandable members 108, 112 may be compliant and malleable allowing deformation and manipulation. Accordingly, they may be rolled or folded to occupy a relatively small volume. Because of this, the prosthetic device 100 may be introduced to the space S of FIG. 2 using virtually any surgical technique including anterior, trans/retro-peritoneal, posterior, trans-lateral, trans-sacral, antero-lateral, transforaminal, among others. In one exemplary embodiment, because the expandable members 108, 112 do not have a fixed geometry during the insertion process, they may be rolled or folded and fitted through a small cannula that provides access to the vertebral space S from a posterior approach. Accordingly, the prosthetic device 100 may be installed through less invasive surgical methods than when using conventional fixed-geometry prosthetic discs.

Prior to insertion, a physician may use a trial to determine the proper height of the intervertebral space. Once determined a prosthetic device 100 configured to obtain the desired height may be selected for placement in the intervertebral space. Accordingly, in some embodiments, a number of different sized inflatable members may be provided for selection to allow a proper fit. In some embodiments, expanding the expandable members 108, 112 may distract the vertebrae. Further, in some of these embodiments, the expandable members may be filled only until the vertebrae are distracted a desired amount.

In some embodiments, the top and bottom portions 102, 104 may be simultaneously placed between the upper and lower vertebrae $V_U$, $V_L$, while in other embodiments, the top and bottom portions 102, 104 are placed at separate times. When placed together, the top and bottom portions 102, 104 may be held together during the placement process to limit any relative movement. An implantation tool (not shown) may be implemented for this purpose. In some embodiments, a resorbable ring may be disposed between the top and bottom portions 102, 104 to locate the portions relative to each other.

Once the prosthetic device 100, including the top portion 102 and bottom portion 104, is placed between adjacent vertebrae, the top and bottom expandable members 108, 112 may be expanded to provide support to the articulation members 106, 110. The top and bottom expandable members 108, 112 may be designed to expand to a specific shape and height. For example, the expandable members 108, 112 may be inelastic so that once the designed shape is obtained, then the shape is maintained. In addition, the expandable members may be designed to expand only to a certain height. In other embodiments, the expandable members may be elastic, allowing the bag to stretch during expansion.

In one aspect, a filling material, such as a biocompatible cement, may be injected to expand the expandable members 108, 112 to their pre-established size and geometry. In a further example, the expandable members 108 may be at least partially filled with granular materials that may provide some level of rigidity. The granular materials may include, for example, beads, granules, bone pastes, bone powders, among others.

Figure 6A:
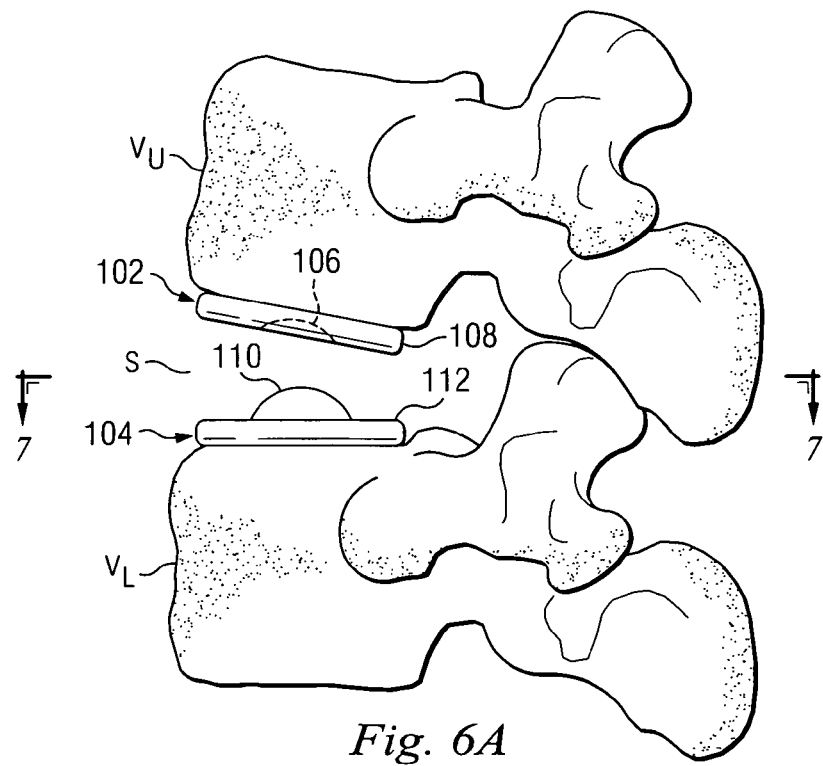
FIGS. 6A and 6B are pictorial representations of an intervertebral prosthetic device disposed between adjacent vertebral bodies.
Figure 6B:
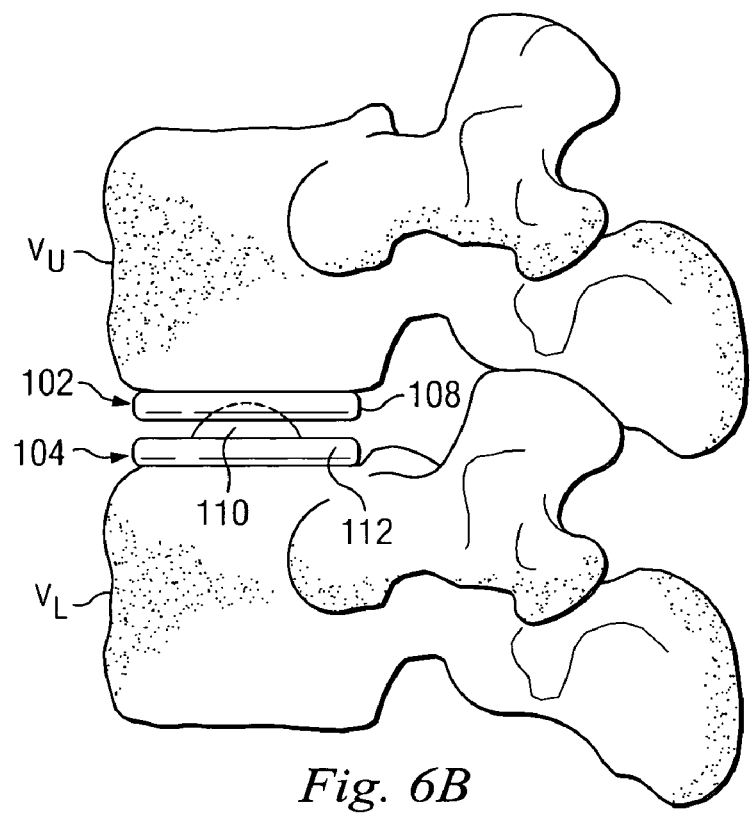
Figure 7:
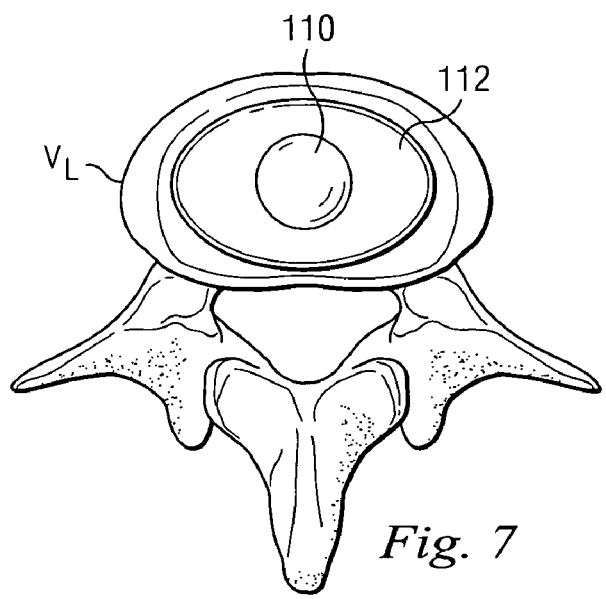
FIG. 7 is a pictorial representation of a top view of a part of the intervertebral prosthetic device of FIG. 6.

FIGS. 6A, 6B, and 7 show one exemplary embodiment of the prosthetic device 100 in an expanded state. When expanded, the expandable members 108, 112 secure the respective articulation members 106, 110 in a position that allows articulation between the upper and lower vertebrae $V_U$, $V_L$. As in FIG. 3, FIG. 6A shows exaggerated vertebrae spacing to provide clarity to the top and bottom portions 102, 104. FIG. 6B, however, shows the vertebrae spaced more conventionally, with the articulation members 106, 110 engaged to provide articulating motion. In the exemplary embodiment shown, the top and bottom articulation members 106, 108 form a ball and socket joint. However, the articulation members also may form a ball and trough joint, a pea and saucer, or other articulating joint. The ball and socket, the ball and trough, and the pea and saucer joints all allow articulation about any axis providing greater degrees of freedom to a patient. In other exemplary embodiments (not shown), the top and bottom articulation members 106, 110 are secured using a pinned joint that forms a hinge allowing articulation in only about a single axis. Other types of joints also may provide articulation to the vertebrae.

The expandable members 108, 112 may be expanded with a filling material that initially is at least partially flowable, but that may harden or be compacted to form a substantially rigid and stiff member. In some exemplary embodiments, the filling material provides support to the articulation members 106, 110 and fixes the expandable members 108, 112 in a specific orientation and geometry.

Figure 8:
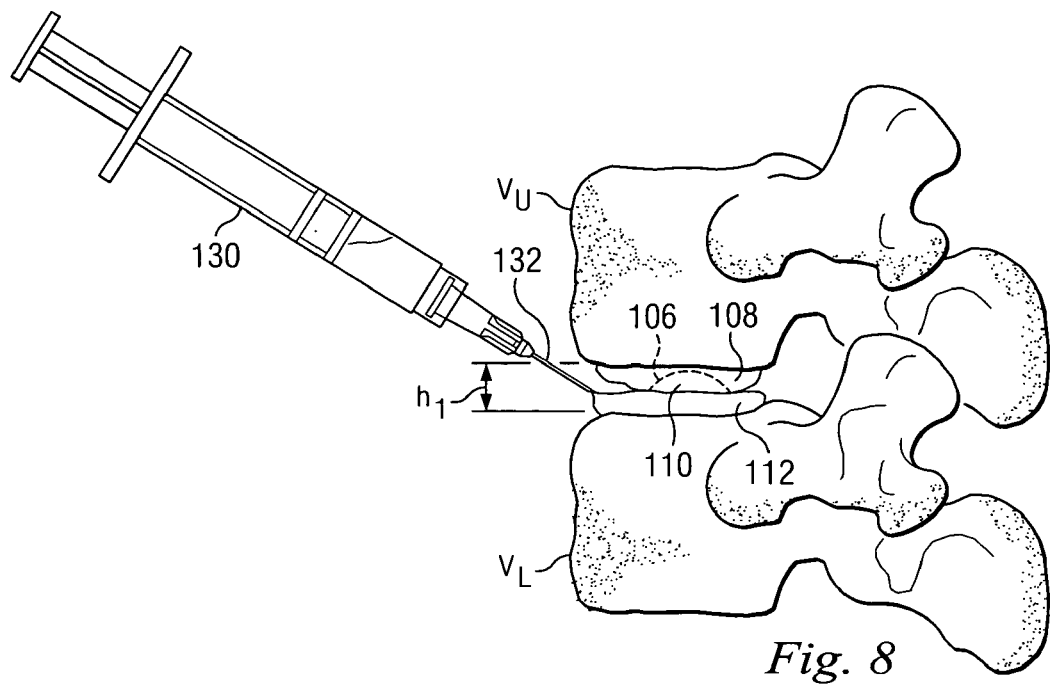
FIGS. 8 through 10 are pictorial representations of systems for expanding the intervertebral prosthetic devices.
Figure 9:
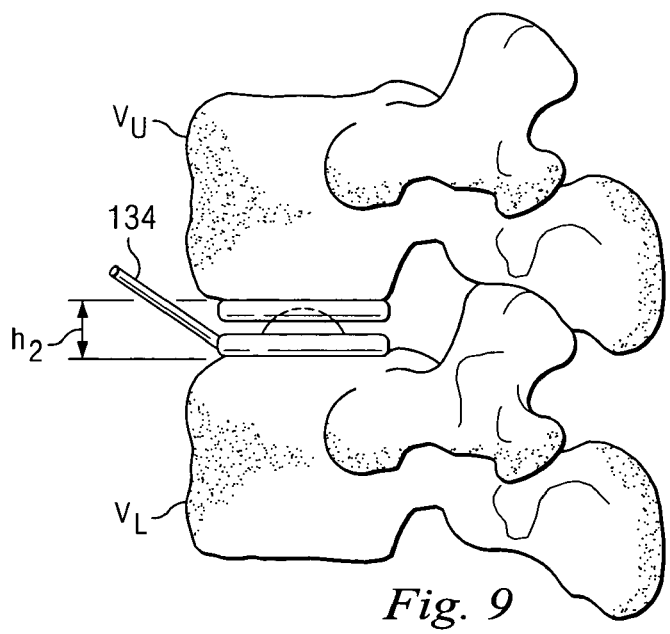
Figure 10:
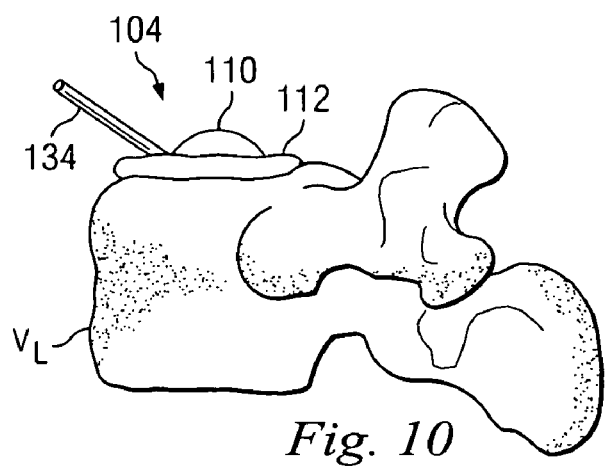

FIGS. 8 through 10 show exemplary systems for filling the expandable members 108, 112. FIG. 8 shows the expandable members 108, 112 in a deflated state. Therefore, although the prosthetic device 100 is disposed between the upper and lower vertebrae $V_U$, $V_L$, the upper and lower vertebrae may be compressed together as shown. Accordingly, when the expandable members 108, 112 are in an unexpanded state, the prosthetic disc 100, as well as the disc space S may have a height represented by $h_1$. Further below, with reference to FIG. 9, height $h_1$ will be compared with a height $h_2$ of the prosthetic disc 100 and the intervertebral disc space where the expandable members 108, 112 are in an expanded state.

In the example shown in FIG. 8, a syringe 130 having a needle 132 may be used to inject the filling material to expand the expandable members 108, 112. The filling material may be in a partially liquid state during injection and may be configured to cure or harden to form a base for the articulation members 106, 110.

In FIG. 9, a substance injector 134 may be used with the expandable members 108, 112 for simple insertion of the filling material. The substance injector 134 in FIG. 9 is shown and described as associated only with the expandable member 112, but a similar injector also may be associated with and used to fill the expandable member 108. The substance injector 134 may be preformed and may be attached to and extend from the expandable member 112. Accordingly, when the expandable members 108, 112 are placed within the intervertebral space S, the substance injector 134 may provide simple access to a physician who will inject the filling material through the substance injector 134 into one or both of the expandable members 108, 112.

In one exemplary embodiment, the substance injector 134 is integral with the expandable member 112 itself, while in another exemplary embodiment, the substance injector 134 is formed of a material attached to the expandable member 112. In yet additional exemplary embodiments, the substance injector 134 may be inserted into the expandable member 112 after the expandable member 112 has been located in the intervertebral space S. Once the expandable member 112 is filled, the substance injector 134 may be removed or disposed in a manner to not interfere with articulation of the device 100 or the spinal column. In some exemplary embodiments, including when the substance injector 134 is removable from the expandable member 112, the substance injector 134 may be configured to be snapped off from the expandable member 112 and removed. Alternatively, the substance injector 134 may be tied off, cut off, or otherwise removed. In one exemplary embodiment, the substance injector 134 is connected with the expandable member 112 and remains in the surgical site with the expandable member 112. The expandable member 108 may be configured similar to the expandable member 112.

FIG. 9 shows the expandable members 108, 112 in an expanded state. Accordingly the prosthetic disc 100 and the intervertebral space have a second height $h_2$. The second height $h_2$ of FIG. 9 may be greater than the first height $h_1$ of FIG. 8 because the expanded members 108, 112 in FIG. 9 contain filling material. Likewise, the first height $h_1$ may be relative smaller than the second height $h_2$, as the expandable members 108, 112 are void of material. In some embodiments, the muscles and ligaments associated with the spinal column may compress the disc space between the upper and lower vertebrae $V_U$, $V_L$ after the natural discal tissue is removed. Once the prosthetic disc 100 is placed within the disc space, the process of filling the expandable members 108, 112 may partially or fully distract the upper and lower vertebrae $V_U$, $V_L$ to the desired disc height. Accordingly, the filling process may distract the upper and lower vertebrae $V_U$, $V_L$ from the first height $h_1$ to the second height $h_2$.

FIG. 10 shows an exemplary embodiment of a substance injector 134 disposed adjacent the articulation member 110. Only the bottom portion 104 is shown being filled in FIG. 10, but it should be understood that the exemplary systems could be used equally with the top portion 102. In this exemplary embodiment, the substance injector 134 may be connected to or removably connected to the articulation member 110. So doing may allow a physician to use the substance injector 134 as a tool to manipulate the position of the articulation member 110 prior to or during injection of the filling material into the expandable member 112. Therefore, the physician may be able to orient the articulation member 110 in its proper location in the vertebral space S. Other methods and systems for placing and moving the articulation member 110 into its desired location also may be used.

The filling material to be injected into the expandable members 108, 112 may be any substance capable of being injected but that will harden to provide sufficient support for the articulation members 106, 110 and to provide support for the vertebrae itself. In some exemplary embodiments, the filling material may be a hardenable material, such as poly-methyl-methacrylate (PMMA) cement or a calcium phosphate cement. In the filling material also may be an injectable elastomeric or polymeric material. The filling material may be un-reinforced or may be reinforced with, for example, carbon or glass fibers or some other strengthening structure. If the material injected is an elastomeric or polymeric material, the material may provide cushioning and additional dampening to the device 100, as well as to the vertebrae.

In some exemplary embodiments, radiographic markers may be introduced into the filling material and the markers may be simultaneously injected with the filling material into the expandable members 108, 112. For example, radiographic beads or wires may be introduced to the filling material. This may simplify later examinations of the prosthetic device 100 by making the device visible when exposed to radiowaves, such as x-rays. In one exemplary embodiment, the filling material introduced into the expandable members 108, 112 may include a radiopaque material, such as, for example, a cement including barium sulfate. In yet another exemplary embodiment, the filling material includes metallic fibers usable as radiopaque markers. In another exemplary embodiment, the expandable members 108, 112 themselves may be formed of and/or may include radiopaque materials. For example, the expandable members may include wires forming a part of the surface of the expandable member. Therefore, after the surgery, the prosthetic device 100 can be viewed and analyzed, if necessary.

In one exemplary embodiment, after placement of the top and bottom portions 102, 104 in the intervertebral space S, surgical tools (not shown) may be employed to hold the articulation members 106, 110 relative to each other in their proper locations while the top and bottom expandable members 108, 112, are filled with the filling material. Then, once the filling material is cured, the surgical tool may be removed to allow articulation between the top and bottom articulation members 106, 110.

In some exemplary embodiments, the articulation members 106, 110 may include additional rigid structures, such as tabs or attachment points that cooperate with the surgical tooling. These structures may provide a grippable surface enabling a physician to manipulate or align the articulation members 106, 110 and to place the entire upper and lower portions 102, 104 of the prosthetic device 100.

Figure 16:
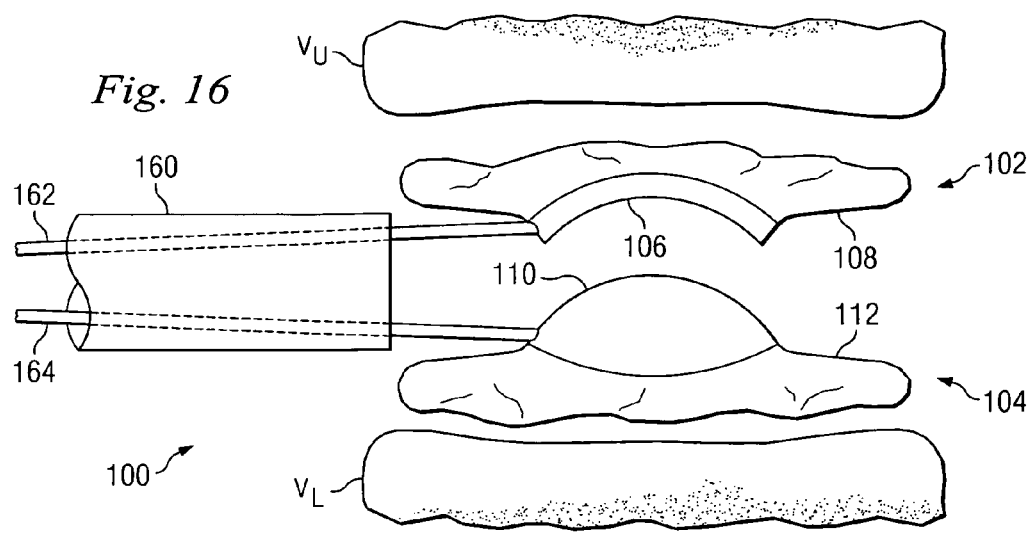
FIGS. 16 and 17 are pictorial representations of a system for placing the intervertebral prosthetic device.
Figure 17:
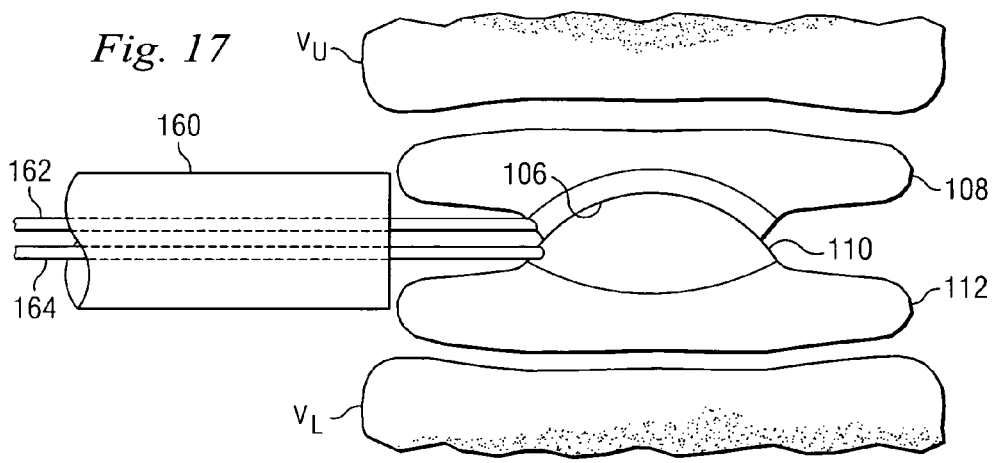

FIGS. 16 and 17 show an example of implanting the prosthetic device 100. As shown, the device 100 may be inserted into an intervertebral disc space through a cannula 160. A connecting means, including one or more instruments, such as a first instrument 162 and a second instrument 164, may connect to the top portion 102 and to the bottom portion 104, respectively. This allows the top and bottom portions 102, 104 to separately pass through the cannula 160 so that the cannula can have a minimal diameter. When in place, the instruments may be manipulated to orient the top and bottom and portions.

In one example, the instruments are aligned adjacent each other to place the top and bottom portions. In other examples, the top and bottom portions 102, 104 may be connected and inserted together using a single instrument or more that one instrument, such as the instruments 162, 164. The instruments 162, 164 may connect at attachment locations formed on the expandable or articulation members or may grip the expandable or articulation members. In one example, the attachment locations may allow the articulation members 106, 110 to snap onto the instruments 162, 164. Once placed, the instruments 162, 164 may attach to each other in a manner to ensure the location of the top portion 102 of the prosthetic device 100 relative to the bottom portion 104. This may be accomplished by meshing the instruments 162, 164, such as by nesting the instruments together, or by configuring them to snap together.

In other examples, the top and bottom portions 102, 104 are placed simultaneously.

Figure 18:
FIG. 18 is a pictorial representation of articulation members connected by a connecting means.

FIG. 18 shows one exemplary embodiment of a connecting means 166 configured to secure the top and bottom articulation members 106, 110 relative to each other. This connecting means 166 may be a clip, a connector, or other system configured to hold the top articulation member 106 relative to the bottom articulation member 110 while the expandable members 108, 112 are filled and manipulated within the disc space. The connecting means 166 may be a rigid support to secure the top and bottom articulation members 106, 110 in place. Once the filling material is sufficiently accomplished, and if necessary, any hardening has began, the connecting means may be removed, allowing articulation of the top and bottom articulation members 106, 110. The connecting means 166 may be used as an alternative or in conjunction with instruments that connect in order to properly position the top and bottom portions 102, 104. Other systems for securing the top portion relative to the bottom portion also could be used.

In some examples, the top and bottom portions 102, 104 are held in place until any cement within the expandable members begins to or completely cures. In other examples, the top and bottom portions 102, 104 are held in place only while the expandable member is filled. Once filled, the top and bottom portions may be manipulated within the disc space to a desired final location.

In another exemplary embodiment, the top and bottom portions 102, 104 may be held in place in the disc space by the upper and lower vertebral bodies themselves, such as might occur with a collapsed disc space. As the expandable members 108, 112 are filled, the height of the disc space may increase. Once the expandable members 108, 112 are sufficiently filled, the articulation members 106, 110 are manipulated into their final position.

In addition to connecting to the articulation members 106, 110, the expandable members 108, 112 also connect with end plate surfaces of the upper and lower vertebrae $V_U$, $V_L$. Conventional prosthetic discs typically incorporate a flat, top or bottom surface that may not always lie flat or flush against the respective upper or lower vertebrae. The prosthetic device 100, however, allows the expandable member 108, 112 to conform in situ to any surface irregularities, bumps, or high spots of the upper and lower vertebrae $V_U$, $V_L$. Accordingly, weight transferred from the vertebrae to the prosthetic device 100 can be distributed over a larger area of the vertebrae, thereby reducing chances of health problems, such as resorption cascade, as well as stress risers and other irregularities that may cause pain to a patient.

FIGS. 11 through 15 disclose several exemplary embodiments of expandable members 108, 112 configured to attach to the upper and lower vertebrae $V_U$, $V_L$. While only the upper expandable member 108 is shown, the lower expandable member 112 may include any of the features described. Preferably, the lower expandable member 112 will have the same features as the upper expandable member 108.

Figure 11:
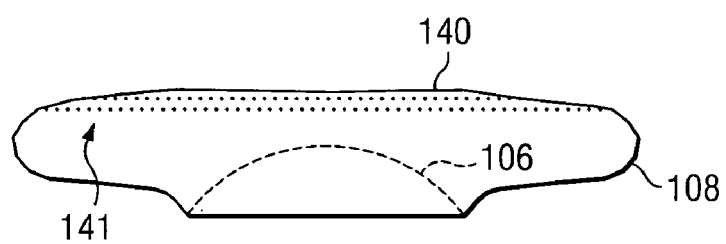
FIGS. 11 through 15 are pictorial representations of exemplary embodiments of intervertebral prosthetic devices.

As shown in FIG. 11, the expandable member 108 may include an upper surface 140 having pores 141 formed therein. The porous upper surface 140 may promote bone ingrowth that over time would allow the bone to grow into and hold the expandable member 108 and the prosthetic disc 100 in place. In one exemplary embodiment, the entire expandable member 108 may be formed of a material providing the porous structure shown in FIG. 11. In another exemplary embodiment, the pores 141 may be created through a treatment of the upper surface 140 of the expandable member 108. For example, in one embodiment, porous material could be sewn or sutured to the top of the expandable member 108, or in a second embodiment, a spray or coating may be applied to the top expandable member 108.

In one exemplary embodiment, the porous surface 140 may be a permeable or a semi-permeable structure allowing a portion of the filling material injected to expand the expandable member 108 and to communicate through the upper surface 140 of the expandable member 108 to assist in attachment to the vertebrae. In one such embodiment, the filling material introducible into the expandable member 108 is a hardenable adhesive. Accordingly, it may permeate through the upper surface 140 of the expandable member 108, affixing the expandable member 108 in place against the vertebrae. Alternatively, the bone and connective tissue may grow through the membrane and interact with the filling material.

Figure 12:
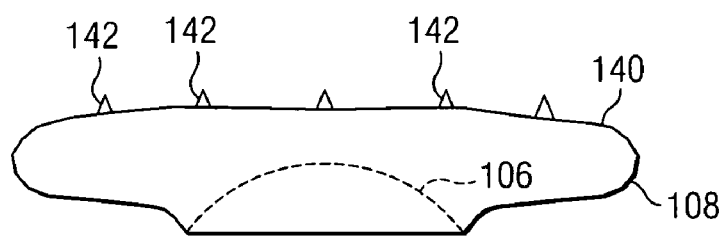

FIG. 12 shows another embodiment of an expandable member 108 securable to a vertebrae. In FIG. 12, projections 142 are preformed onto the upper surface 140 of the expandable member 108. These projections 142 may engage the vertebrae when the expandable member 108 is filled with the filling material, with the filling material providing the force to drive the projections 142 into the vertebrae. The projections 142 may be integrally formed with the expandable member 108 of the same material as the expandable member 108 or alternatively, may be secured to the expandable member 108 using an adhesive or cement. In another exemplary embodiment, the projections 142 include securing pins that may penetrate the top surface of the expandable member 108, and may be attached to the interior of the expandable member 108, thereby securing the projections 142 in place on the expandable member 108. In FIG. 12, the projections 142 are shown as spikes extending from the surface 140 of the expandable member 108. However, the projections 142 could be any shape having, for example, a pointed, tapered, or a flat upper surface spaced from the upper surface of the expandable member 108, that is configured to engage the vertebrae.

Figure 13:
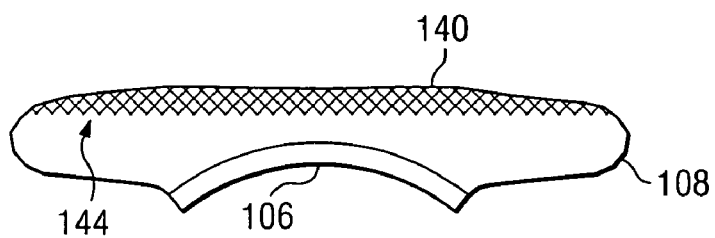

FIG. 13 shows an exemplary expandable member 108 having a coating 144 on its upper surface 140 that may promote integration or bone growth into the expandable member 108. For example, the bone-growth coating may be, for example, a hydroxyapatite coating formed of calcium phosphate, a biologic substance such as BMP or other substance, or other material may be applied to the upper surface 140 of the expandable member 108. In FIG. 13, the top articulation member 106 is a trough rather than a ball socket. As explained above, the articulation members could have any of a variety different configurations providing articulating motion to the vertebral joint.

Figure 14:
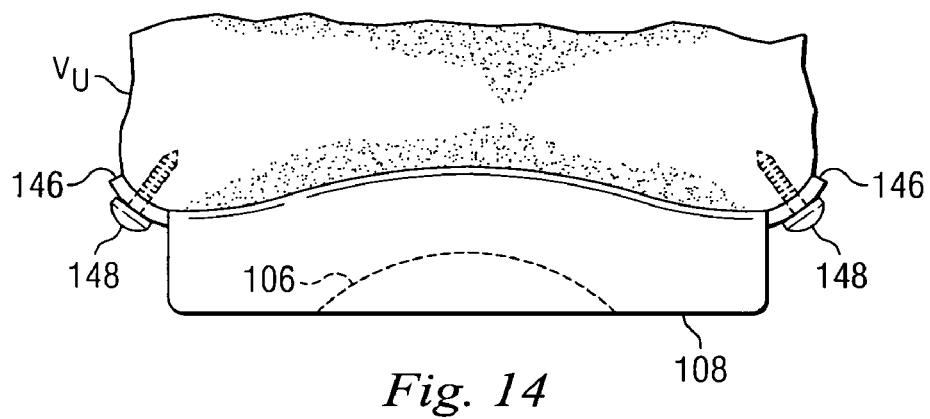

FIG. 14 shows yet another exemplary system for attaching the expandable member 108 to the vertebrae V. In FIG. 14, the expandable member 108 includes a seam or skirt 146 about its edge. Using the seam or skirt 146, stakes 148 such as, for example, screws, spikes, or projections, may be used to stake the expandable member 108 against the vertebrae $V_U$. The stakes 148 may be driven through the skirt 146 about the edge of the expandable member 108 and into the vertebrae $V_U$, securing the expandable member 108 in place against the vertebrae $V_U$.

Figure 15:
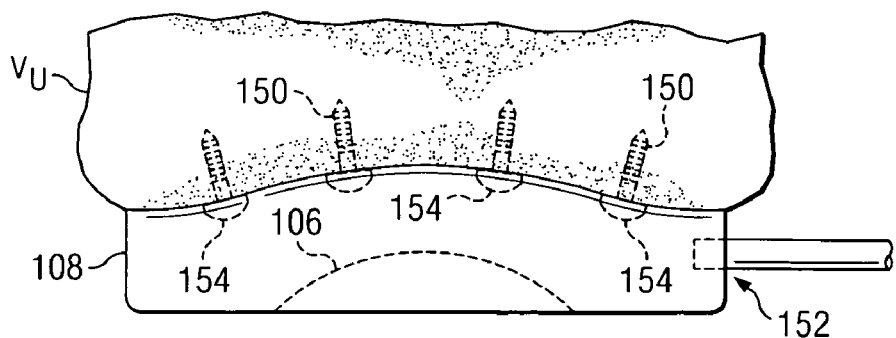

FIG. 15 shows another exemplary system for attaching the expandable member 108 to the vertebra $V_U$. In FIG. 15, prior to filling the expandable member 108 with a filling material, tacks or pins 150 may be introduced to an interior of the expandable member 108 through a port 152. The port 152 may be associated with the substance injector or other cannula. From the interior of the expandable member 108, the tacks 150 may be driven through the upper surface 140 of the expandable member 108 and into the vertebra $V_U$. In one exemplary embodiment, the tacks 150 are inserted through the port 152 into the interior, then rotated 90 degrees to orient the pointed end, and then driven into the vertebra $V_U$. Heads 154 on the tacks 150 may hold the top surface 140 of the expandable member 108 against the vertebra $V_U$. Once those tacks 150 are in place, filling the expandable member 108 with the filling material may apply pressure on the heads 154, driving the tacks 150 further into the vertebra and securing the expandable member 108 against the vertebra $V_U$.

Figure 19:
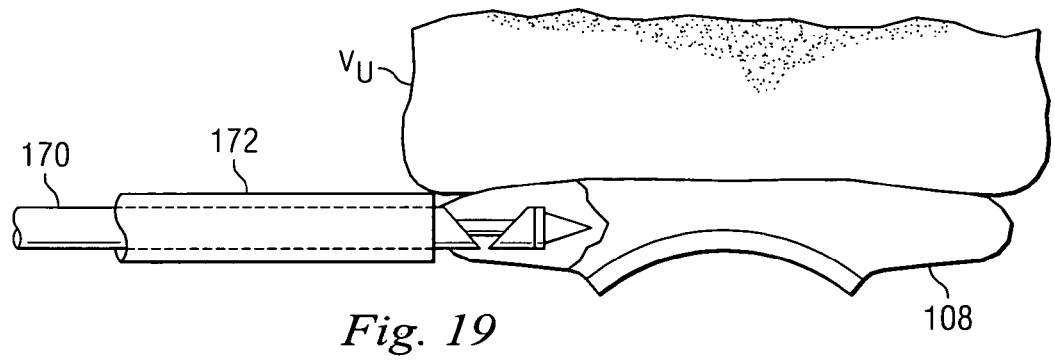
FIGS. 19, 20A, 20B, and 21 are pictorial representations of an instrument used to implant the intervertebral prosthetic device.

FIGS. 19, 20A, 20B, and 21 show one example of introducing tacks 150 into the expandable member 108 to attach the expandable member to a vertebra as shown in FIG. 15. With reference to FIG. 19, an insertion tool 70 is introduced through an insertion tube 72 into the expandable member 108. As shown in FIGS. 19A and 19B, the insertion tool 70 includes a distal end 174 configured to attached to the tack 150 and a proximal end (not shown) configured to be manipulated by a surgeon. The insertion tool 70 may be configured with a rotation means 176, such as, for example, a hinge, a compliant member, or a flexible member, that allows the distal end 174 to rotate the tack 150 toward the vertebral endplate. In the example shown, the distal end is configured to rotate 90 degrees.

Figure 20A:
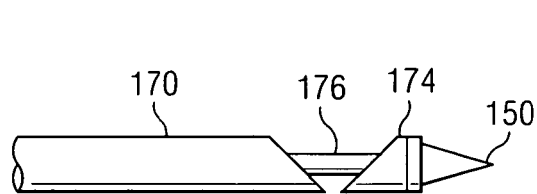
Figure 20B:
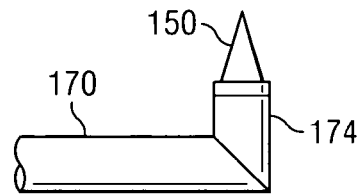
Figure 21:
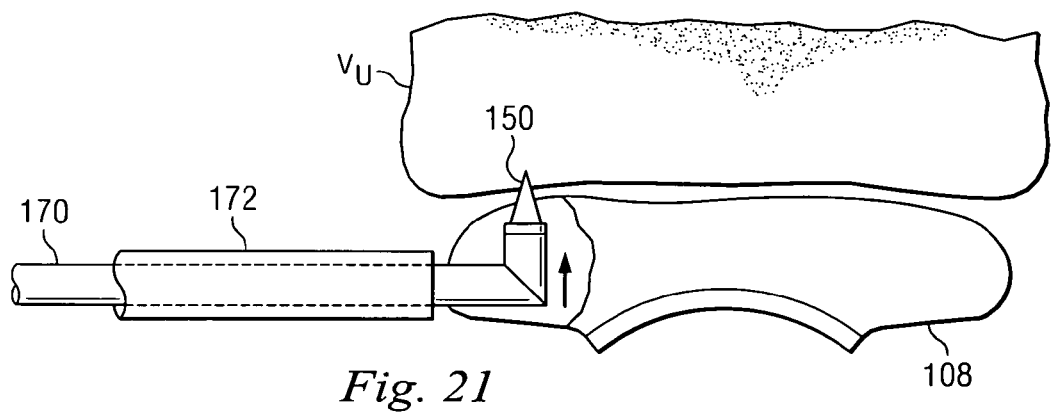

FIG. 20A shows the insertion tool 170 and tack 150 in a position for insertion through the insertion tube 172, and FIG. 20B shows the insertion tool 170 and tack 150 rotated to allow the tack 150 to be driven into the vertebra. FIG. 21 shows the manipulated tack 150 and insertion tool 170 within the inflatable member 108. Once placed, the articulation members may still be manipulated within the disc space so that they are located to provide an ideal center of rotation.

Because of its convenient nature, suppliers of the prosthetic device 100 may sell the device in a kit. A kit may include, for example, the prosthetic device 100 with its articulation members 106, 108 and its expandable members 110, 112. The filling material, as described above, also may be part of the kit. Other combinations could also be used.

The prosthetic device 100 described herein may be placed and fitted into an intervertebral space S in an un-expanded state. To place the device 100, a physician may form an introductory cavity or access to the damaged or degenerated disc. Using methods known in the art, the physician may remove all or part of the disc. The physician may then introduce the top and bottom portions 102, 104 of the prosthetic device 100 to the disc space, either together or one at a time.

Because the upper and lower portions 102, 104 may be introduced in an un-expanded state, the upper and lower portions 102, 104 may have a smaller profile and geometry than conventional prosthetic discs. Accordingly, introducing the upper and lower portions 102, 104 may be performed from not only an anterior direction, but also from other directions, such as a posterior or lateral direction. In one exemplary embodiment, the expandable members 108, 112 of the upper and lower portions 102, 104 are rolled to form a small profile during introduction. When the upper or lower portions 102, 104 are disposed in the vertebral space S between adjacent vertebrae, the expandable members 108, 112 may be adjusted and placed so that the attached articulation members 106, 110 are disposed in a proper position. Adjusting the expandable members 108, 112 may include unrolling the expandable members 108, 112 and aligning the articulation members 106, 110 by manipulating the attached substance injector 134. In some exemplary embodiments, the expandable member may be pinned or staked to the adjacent vertebrae.

Once the articulation members are aligned, a filling material may be introduced to the expandable members 108, 112, expanding them to their pre-established size and shape. In one exemplary embodiment, the articulation members 106, 110 may be held in place by a tool while the filling material is introduced. In some embodiments, expanding the expandable members 108, 112 may distract the vertebrae a desired distance to provide the properly sized disc space. Also, in some embodiments, expanding the expandable members 108, 112 may drive projections or pins or other attachment systems into contact with the vertebrae. In the embodiments where the filling material hardens and has achieved a desired hardness level, in some embodiments, the substance injector may be removed from the expandable member.

The smaller profile and manipulatable profile of the prosthetic device 100 may allow the device to be insertable from a number of different directions. Accordingly, the surgical process may be less invasive and less complex. This may reduce recovery time and may simplify subsequent surgeries, should they become necessary.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. It is understood that all spatial references, such as "upper" and "lower," are for illustrative purposes only and can be varied within the scope of the disclosure.

We claim:

1. A prosthetic device for insertion into an intervertebral space defined by adjacent vertebrae, comprising:
    a first articulation member having a first articulating surface and a first attachment surface;
    a second articulation member having a second articulating surface and a second attachment surface, the second articulating surface being configured to cooperate with the first articulating surface to permit articulating motion;
    a connection means extending between the first and second articulation members for rigidly securing the first and second articulation members to one another, the connection means sized and shaped to allow insertion of the first and second articulating members within the intervertebral space with the connection means extending between and securing the first and second articulation members in a fixed orientation with respect to each other, the connection means removable to permit articulating motion between the first and second articulation members;
    an expandable member connected to the first articulation member and configured to support and position the first articulation member within the intervertebral space, the expandable member having a cavity for receiving a filling material;
    a plurality of tacks separate from the expandable member, each of the plurality of tacks sized and shaped for introduction into the cavity of the expandable member and through a wall of the expandable member defining the cavity into one of the adjacent vertebrae to secure the expandable member to the vertebra; and
    a substance injector associated with at least one of the first and second articulation members and being sized and shaped to introduce a filling material into the expandable member to expand the expandable member, the filling material exerting a pressure on the plurality of tacks to secure the tacks into one of the adjacent vertebrae.

2. The prosthetic device of claim 1, wherein the substance injector is integral with the expandable member.

3. The prosthetic device of claim 1, wherein the substance injector is removably secured to the expandable member.

4. The prosthetic device of claim 1, wherein the substance injector sized and shaped to position the first and second articulating members within the intervertebral space after the connection means is removed.

5. A kit for a prosthetic device for insertion into an intervertebral space defined by adjacent vertebrae, comprising:
    a first articulation member having a first articulating surface and a first attachment surface;
    a first expandable member connected to the first articulation member and configured to support and position the first articulation member within the intervertebral space, the first expandable member having a cavity for receiving a filling material;
    a second articulation member having a second articulating surface and a second attachment surface, the second articulating surface being configured to cooperate with the first articulating surface to permit articulating motion between the first and second articulation members;
    a second expandable member connected to the second articulation member and configured to support and position the second articulation member within the intervertebral space;
    a plurality of tacks separate from the first and second expandable members, each of the plurality of tacks sized and shaped for introduction into and through the cavity of the first expandable member and into the adjacent vertebra to secure the first expandable member to the adjacent vertebra;
    a filling material for introduction into the first and second expandable members;
    a cannula for introducing the filling material into the first and second expandable members; and
    an insertion tool for inserting the plurality of tacks into and through the cavity of the first expandable member, the insertion tool comprising a distal portion for securely holding at least one of the plurality of tacks and a rotation means for selectively rotating the distal portion within the cavity 90 degrees between an insertion configuration for introducing the at least one of the plurality of tacks into the first expandable member and an anchoring configuration for introducing the at least one of the plurality of tacks through the first expandable member and into the adjacent vertebra.

6. The kit of claim 5, wherein the rotation means for selectively rotating the distal portion between the insertion configuration and the anchoring configuration comprises a hinge joint.

7. The kit of claim 5, further comprising a removable connecting means for securing the first and second articulation members relative to one other, the removable connecting means sized and shaped for securing the first and second articulation members in a fixed position relative to each other within the intervertebral space during inflation of the expandable member.

8. The kit of claim 7, wherein the removable connecting means comprises a clip removably attached to each of the first and second articulation members.

9. The kit of claim 7, wherein the removable connecting means comprises a first instrument configured to connect to the first articulation member and a second instrument configured to connect to the second articulation member, wherein the first and second instruments are attachable to one another in order to position the first articulation member relative to the second articulation member in a desired orientation.

10. A system for relieving back pain comprising:
- a prosthetic device for insertion into an intervertebral space defined by adjacent vertebrae, including:
  - a first articulation member having a first articulating surface and a first attachment surface;
  - a second articulation member having a second articulating surface and a second attachment surface, the second articulating surface being configured to cooperate with the first articulating surface to permit articulating motion; and
  - an expandable member having a cavity and connected to the first articulation member and configured to support and position the first articulation member within the intervertebral space;
- a substance injector associated with at least one of the first and second articulation members and being sized and shaped to introduce a flowable media into the expandable member to expand the expandable member;
- a plurality of tacks separate from the expandable member, each of the plurality of tacks sized and shaped for introduction through the substance injector and into the cavity of the expandable member such that the flowable media exerts a pressure on the plurality of tacks into one of the adjacent vertebrae to secure the expandable member to the vertebra; and
- connecting means sized and shaped to selectively secure and position the first articulation member relative to the second articulation member, thereby selectively limiting the articulating motion permitted between the first and second articulation members within the intervertebral space.

11. The system of claim 10, wherein the connecting means is a clip removably connected to each of the first and second articulation members.

12. The system of claim 10, wherein the connecting means includes a first and a second instrument.

13. The system of claim 12, wherein the first instrument is configured to connect to the first articulation member and the second instrument is configured to connect to the second articulation member.

14. The system of claim 13, wherein the first and second instruments are configured to attach together to locate the first articulation member relative to the second articulation member.

* * * * *